(12) United States Patent
Hyde et al.

(10) Patent No.: US 7,942,784 B1
(45) Date of Patent: May 17, 2011

(54) SPORTS SPECIFIC TRAINING PROGRAM APPLICATION

(76) Inventors: Len Hyde, Roseville, CA (US); Christopher Amaral, Folsom, CA (US); Jeffrey Stilz, Natomas, CA (US); Davin Johnson, Rocklin, CA (US)

( * ) Notice: Subject to any disclaimer, the term of this patent is extended or adjusted under 35 U.S.C. 154(b) by 0 days.

(21) Appl. No.: 12/796,486

(22) Filed: Jun. 8, 2010

Related U.S. Application Data

(60) Provisional application No. 61/186,412, filed on Jun. 12, 2009.

(51) Int. Cl.
*A63B 71/00* (2006.01)

(52) U.S. Cl. .................... 482/9; 482/1; 482/8; 482/901; 434/247

(58) Field of Classification Search .................. 482/1–9, 482/900–902; 434/247; 73/379.01–379.04; 601/23
See application file for complete search history.

(56) References Cited

U.S. PATENT DOCUMENTS

| | | | | |
|---|---|---|---|---|
| 5,469,740 A | * | 11/1995 | French et al. | 73/379.04 |
| 7,618,347 B2 | * | 11/2009 | Yeo et al. | 482/8 |
| 7,717,827 B2 | * | 5/2010 | Kurunmaki et al. | 482/8 |
| 7,785,232 B2 | * | 8/2010 | Cole et al. | 482/5 |

* cited by examiner

*Primary Examiner* — Glenn Richman
(74) *Attorney, Agent, or Firm* — Neustel Law Offices

(57) ABSTRACT

A sports specific training program application for creating a customizable training program for an athlete of a particular sport. The sports specific training program application includes a user interface preferably connected to and accessible through a network, the user interface allows a user to input user information to correlate with a particular athletic event into one or more user databases. The user information is matched with targeted exercises from an exercise database using training program logic and the resultant training program is outputted to the user, wherein the training program may be outputted in online, printed, or electronic file formats. The user may also input results from performing the training program into the user interface to receive a scorecard of processed results which details progress and history of the user's exercises and goals and for developing subsequent training programs. The present invention may be a stand-alone program without the network.

20 Claims, 5 Drawing Sheets

SPORTS SPECIFIC TRAINING PROGRAM APPLICATION

CROSS REFERENCE TO RELATED APPLICATIONS

I hereby claim benefit under Title 35, United States Code, Section 119(e) of U.S. provisional patent application Ser. No. 61/186,412 filed Jun. 12, 2009. The 61/186,412 application is hereby incorporated by reference into this application.

STATEMENT REGARDING FEDERALLY SPONSORED RESEARCH OR DEVELOPMENT

Not applicable to this application.

BACKGROUND OF THE INVENTION

1. Field of the Invention

The present invention relates generally to an exercise and training program and more specifically it relates to a sports specific training program application for efficiently creating a customizable training program for an athlete of a particular sport which is accessible via online and can be viewed in various formats.

2. Description of the Related Art

Any discussion of the related art throughout the specification should in no way be considered as an admission that such related art is widely known or forms part of common general knowledge in the field.

Sports specific training and exercise programs have been widely used in the past. However, because of the wide array of individual skill and fitness levels, body traits, schedules, and the different sports which require varying levels of experience, skill and aptitude, the training programs generally do not effectively adapt to the particular user's needs and can thus be unfulfilling or largely unproductive for the user.

One way in which the lack of customized training programs has been overcome is by hiring a personal trainer to customize a specific training program, and monitor the athlete's progress through the program. However, hiring a personal trainer is often times be overly expensive and time restrictive for most individuals. Because of the inherent problems with the related art, there is a need for a new and improved sports specific training program application for efficiently creating dynamic customizable and personalized training programs for an athlete of a particular sport, which is accessible via online and can be viewed in various formats.

BRIEF SUMMARY OF THE INVENTION

A system for efficiently creating a customizable training program for an athlete of a particular sport which is accessible via online and can be viewed in various formats. The invention generally relates to an exercise and sports training program which includes a user interface connected to and accessible through a network, the user interface allows a user to input user information to correlate with a particular athletic event into one or more user databases. The user information is matched with targeted exercises from an exercise database using training program logic and the resultant training program is outputted to the user, wherein the training program may be outputted in online, printed, or electronic file formats. The user may also input results from performing the training program into the user interface to receive a scorecard which details progress and history of the user's exercises and goals. The input results are also significant in determining future training programs for a particular user and modifying the training program.

There has thus been outlined, rather broadly, some of the features of the invention in order that the detailed description thereof may be better understood, and in order that the present contribution to the art may be better appreciated. There are additional features of the invention that will be described hereinafter and that will form the subject matter of the claims appended hereto. In this respect, before explaining at least one embodiment of the invention in detail, it is to be understood that the invention is not limited in its application to the details of construction or to the arrangements of the components set forth in the following description or illustrated in the drawings. The invention is capable of other embodiments and of being practiced and carried out in various ways. Also, it is to be understood that the phraseology and terminology employed herein are for the purpose of the description and should not be regarded as limiting.

BRIEF DESCRIPTION OF THE DRAWINGS

Various other objects, features and attendant advantages of the present invention will become fully appreciated as the same becomes better understood when considered in conjunction with the accompanying drawings, in which like reference characters designate the same or similar parts throughout the several views, and wherein.

DETAILED DESCRIPTION OF THE INVENTION

Figure 1:
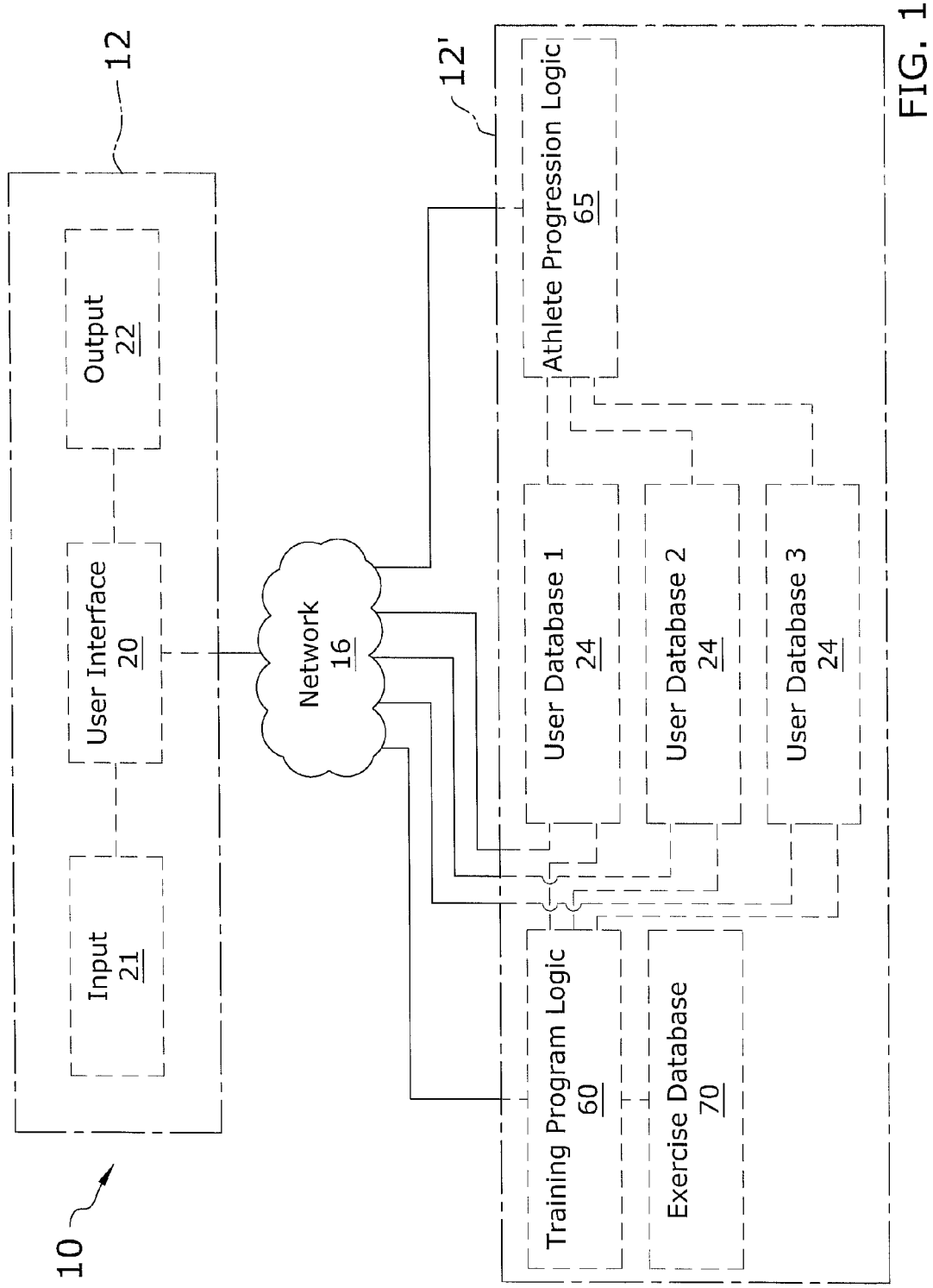
FIG. 1 is an exemplary diagram view of the present invention with a network.

The following description is presented to enable any person skilled in the art to make and use the invention, and is provided in the context of a particular application and its requirements. Various modifications to the disclosed embodiments will be readily apparent to those skilled in the art, and the general principles defined herein may be applied to other embodiments and applications without departing from the spirit and scope of the present invention. Thus, the present invention is not intended to be limited to the embodiments shown, but is to be accorded the widest scope consistent with the principles and features disclosed herein.

The data structures and code described in this detailed description are typically stored on a computer readable storage medium, which may be any device or medium that can store code and/or data for use by a computer system. This includes, but is not limited to, magnetic and optical storage devices such as disk drives, magnetic tape, CDs (compact discs), DVDs (digital video discs), and computer instruction signals embodied in a transmission medium (with or without a carrier wave upon which the signals are modulated). For example, the transmission medium may include a communications network, such as the Internet.

The present invention may be embodied within various languages and technologies such as but not limited to JAVA, JAVASCRIPT, JSCRIPT, WMLSCRIPT, ACTIVEX, CGI, scripts, plug-ins, BASIC, VISUAL BASIC, C, C++, COBOL, FORTRAN, ADA, HTML, DHTML, XML, SGML, WML, HDML, FLASH, SHOCKWAVE, GIF, JPEG, ADOBE ACROBAT, PDF, MICROSOFT WORD, and PASCAL. The present invention may be operated upon various operating systems such as but not limited to UNIX, MACINTOSH, LINUX, WINDOWS, PALMOS, EPOC, WINDOWS CE, FLEXOS, OS/9, and JAVAOS.

Turning now descriptively to the drawings, in which similar reference characters denote similar elements throughout the several views, FIGS. 1 through 5 illustrate a sports specific training program application 10, which comprises a user interface 20 preferably connected to and accessible through a network 16, the user interface 20 allows a user to input user information 21 to correlate with a particular athletic event into one or more user databases 24. The user information 21 is matched with targeted exercises from an exercise database 70 using training program logic 60 and the resultant training program 80 is outputted to the user, wherein the training program 80 may be outputted in online, printed, or electronic file formats. The outputted information 22 may comprise the training program 80 and/or the scorecard 90.

Figure 2:
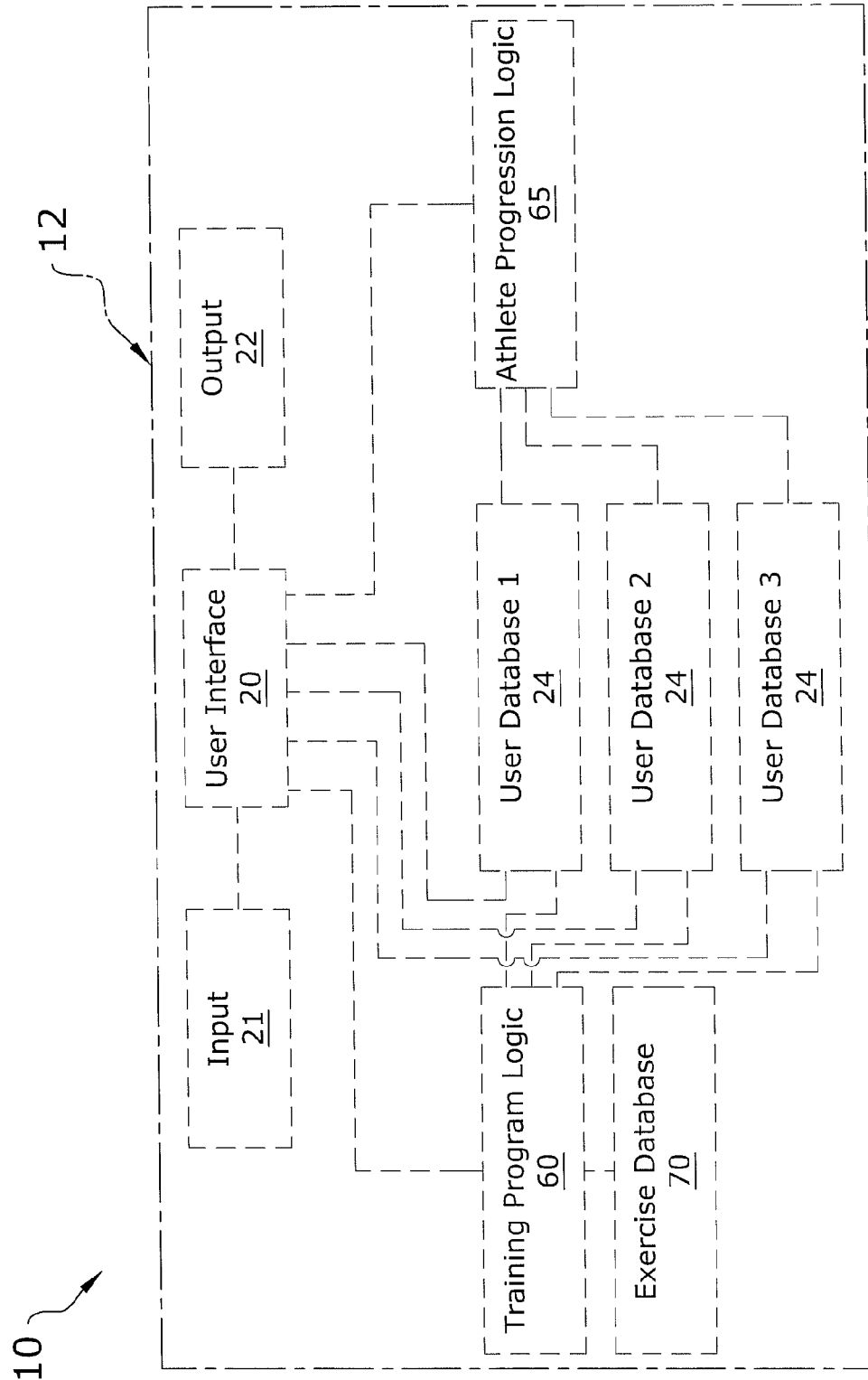
FIG. 2 is an exemplary diagram view of the present invention without a network.

The inputted information 21 may also include input results 40 from performing the training program 80 which are entered into the user interface 20 to receive a scorecard 90 which details progress and history of the user's exercises and goals. It is appreciated that the term exercise may refer to traditional exercise, sport training, sport studying, or any activity which is needed to reach a certain goal, particularly associated with a sport. The present invention is generally utilized by members or subscribers and may include a payment system as appreciated. It is also appreciated that the present invention may be located on a single computer system 12, thus sold in a stand-alone software embodiment and not necessarily be connected to a network 16 as illustrated in FIG. 2.

As illustrated in FIG. 1, the present invention may be employed upon various computer systems 12, 12' all which are preferably connected through a network 16, such as a local network or a global network, such as the Internet. The communications between the computer systems 12, 12' may be accomplished via various methods such as but not limited to wireless, Ethernet, cable, direct connection, telephone lines, and satellite.

The present invention may also be utilized upon global computer networks, local area networks (LAN), wide area networks (WAN), campus area networks (CAN), metropolitan-area networks (MAN), and home area networks (HAN). Various protocols may be utilized by the electronic devices for communications such as but not limited to HTTP, SMTP, FTP and WAP (Wireless Application Protocol). The present invention may be implemented upon various wireless networks such as but not limited to CDPD, CDMA, GSM, PDC, PHS, TDMA, FLEX, REFLEX, IDEN, TETRA, DECT, DATATAC, and MOBITEX. The present invention may also be utilized with online services and internet service providers such as AMERICA ONLINE (AOL), COMPUSERVE, WEBTV, and MSN INTERNET SERVICES. The present invention preferably utilizes the Internet 16 for transmitting data, however it can be appreciated that as future technologies are created that various aspects of the invention may be practiced with these improved technologies.

The present invention may be implemented and viewed upon various types and brands of web/e-mail browsers such as but not limited to MICROSOFT INTERNET EXPLORER, NETSCAPE NAVIGATOR, OPERA, AMAYA, ARENA, LYNX, HOTJAVA, MOZILLA, ICAB, MICROSOFT OUTLOOK, and MICROSOFT OUTLOOK EXPRESS. Browsers for handheld wireless devices, often times referred to as "microbrowsers", are also capable of implementing the present invention. A browser is typically capable of displaying/playing various types of content including but not limited text, graphic, audio and multimedia.

The user databases 24 and exercise database 70 are illustrated upon different computer systems 12, 12' in FIG. 1; however it is appreciated that this is simply for illustrative purposes and the computer systems 12, 12' may be integrated, such as by using a single computer system 12 to store information and perform logic commands. It can be appreciated that the computer system 12 and/or 12' may be comprised of various other electronic devices including but not limited to mobile phones, telephones, personal digital assistants (PDAs), handheld wireless devices, two-way radios, smart phones, communicators, video viewing units, television units, television receivers, cable television receivers, pagers, communication devices, storage servers, and digital satellite receiver units. Additional computer systems may be used, such as a computer system for each database 24, 70 or logic program 60, 65.

The inputted information 21 to the user interface allows the user to enter in various user information 30, 40 and results 50 of exercises performed. The user interface 20 allows input through various types of peripheral devices, such as a keyboard, pointing devices such as a computer mouse, a track ball, a stylus, a tablet to manipulate a pointer on a screen of the computer system, or various other peripheral devices. The peripheral devices are common in the art and for that reason are not shown.

Each user's inputted information may be stored within a user database 24. Each user may have their own user database 24 for all inputted information or each user may have separate user databases 24 for separate types of inputted information. Alternately, one database 24 may be used for all types of information. Various means to store, record, and access information may be employed with the user databases 24 as appreciated. Each user database 24 is preferably connected to the network 16 and is accessible via the network 16 through the user interface 20 and by the training program logic 60 and athlete progressive logic 65.

Figure 3:
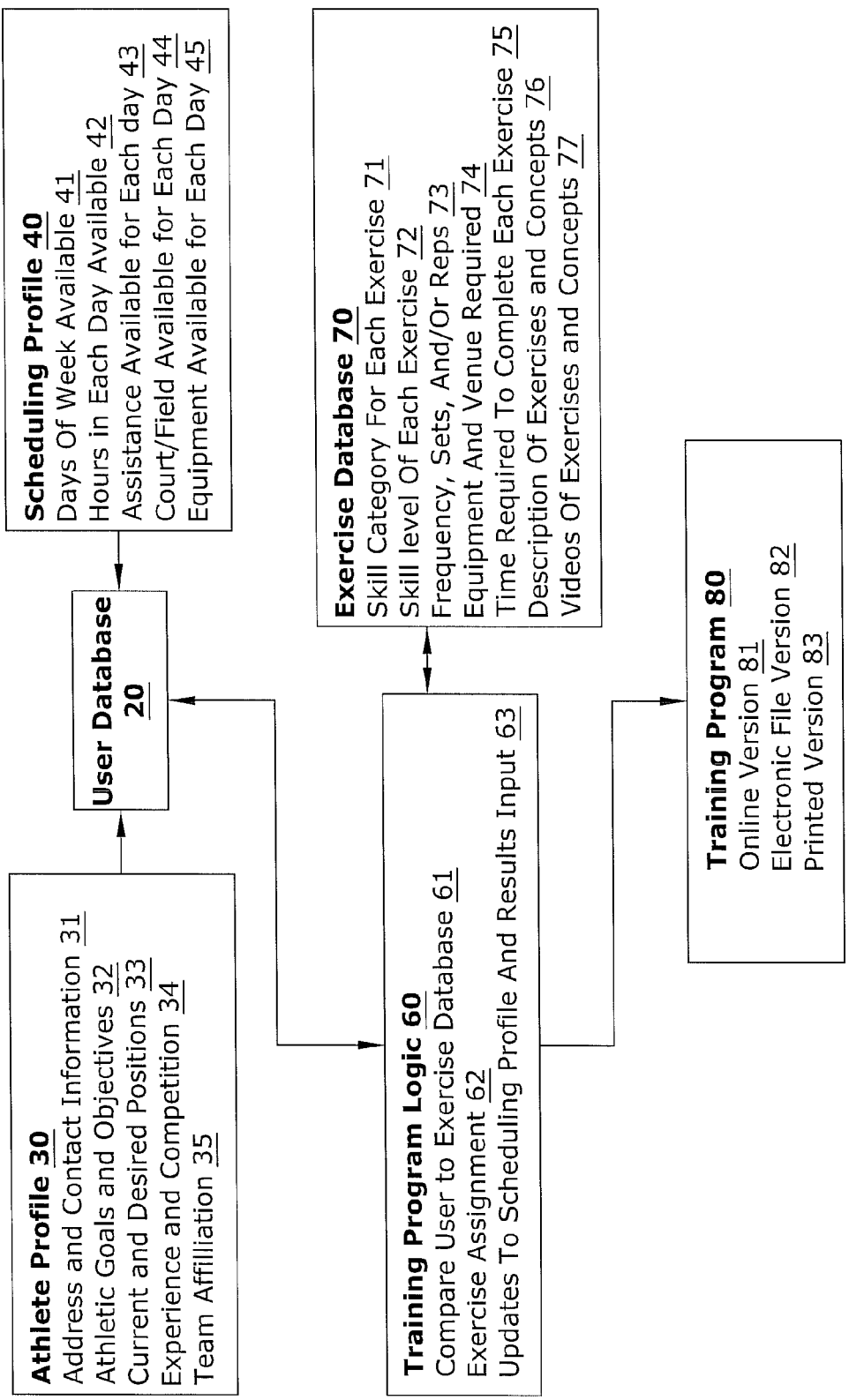
FIG. 3 is a block diagram of the method of utilizing the training program.

One type of inputted information 21 used by the user and stored in the user database 24 is the inputted user information which generally includes information relating to an athlete profile 30 and a scheduling profile 40 as illustrated in FIG. 3. The athlete's profile 30 may include sections for address and contact information 31 of the user, athletic goals and objectives 32 of the user, current and desired positions 33 of the user, experience and competition level 34 of the user, and team affiliation 35 of the user. Each section 31-35 generally relates to a particular sport that the user is training for, such as the sport position the user plays, the experience level of the user in the particular sport, etc. It is appreciated that various other criteria may be included in the athlete's profile 30.

As illustrated in FIG. 3, the scheduling profile 40 generally includes sections for days of the week that the user is available for exercise and training 21, the number of hours in each available day that the user can exercise and train 42, assistance available for each day 43, court/field or training venue available days 44, and training and exercise equipment available days 45. It is appreciated that various other criteria may be included in the scheduling profile 40. Both of the athlete profile 30 and the scheduling profile 40 may allow for real time editing and updating.

The training program logic 60 generally includes any type of codes, formulas, commands, etc. to match the information from the user database 24 to the correlating exercises from the exercise database 70. It is appreciated that the training program logic 60 may be broken down into various sectors for particular tasks. Additionally, schedule profile and training results are utilized in the training program logic 60. The training program 80 may further classify each athlete according to a particular level, such as beginner, intermediate, proficient, superior, and master.

The training program logic 60 may include a first section 61 for comparing the user database 24 to the exercise database 70, a section 62 for assigning matched exercises to the calendar according to user and venue availability as deemed by the scheduling profile 40, section 63 for updating to scheduling profile 40 and results input 50, and fitness or training area of emphasis, etc. It is appreciated that various other criteria may be included in the training program logic 60. It is also appreciated that the training program logic 60 may use some or all of the inputted information 21 depending upon the particular request from the user.

The exercise database 70 which is generally in communication with the training program logic 60 includes a plurality of stored exercises and training methods each with a set of instructions (if necessary) on how to perform the exercise or training method. Each of the exercises or training methods is also tailored to a specific muscle group, sports skill category, athletic position, sport, etc. to be matched with the athlete profile 30 and scheduling profile 40 of the user information. Such instructions stored within the exercise database for each exercise may include skill category and subgroup for each exercise 71, skill level and difficulty of each exercise 72, recommended frequency, sets and/or reps for the exercise 73, assistance, equipment court/field required for each exercise 74, time required to complete each exercise 75. Each exercise information may also include videos, written, and/or pictorial examples of how to perform the exercise, attributes of the exercise, etc. The exercise database 70 also includes video demonstrations and detailed exercise descriptions as noted by numeral 77.

The recommended exercises are communicated to the training program 80 which communicates the exercises either via in online format 81 through the network 16, a downloadable electronic file format 82, or a printed format 83. The training program 80 may also include pictures, descriptions, videos, tutorials, step-by-step instructions, focus points, etc. all which communicate how to perform the recommended exercise to the recommended specifications. Depending upon how an athlete does in a particular drill, the training program 80 may want assign more or less of similar drills for subsequent training periods. Thus, the training program 80 directly communicates with the results input 50 to determine progression and status of exercise drills by the athlete. The results from the results input 50 are key factors in building subsequent training programs for the athlete.

Figure 4:
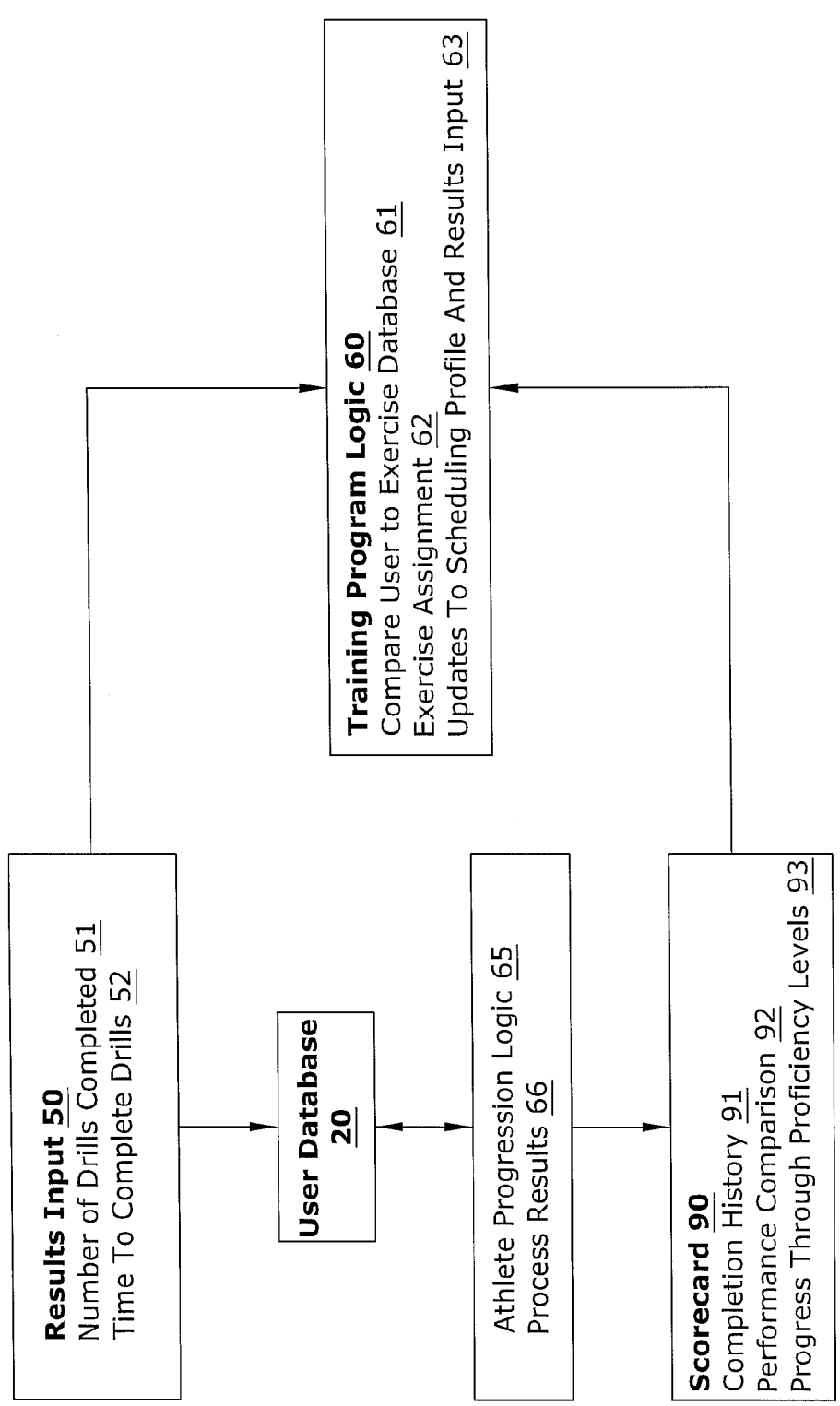
FIG. 4 is a block diagram of the method of displaying exercise results.
Figure 5:
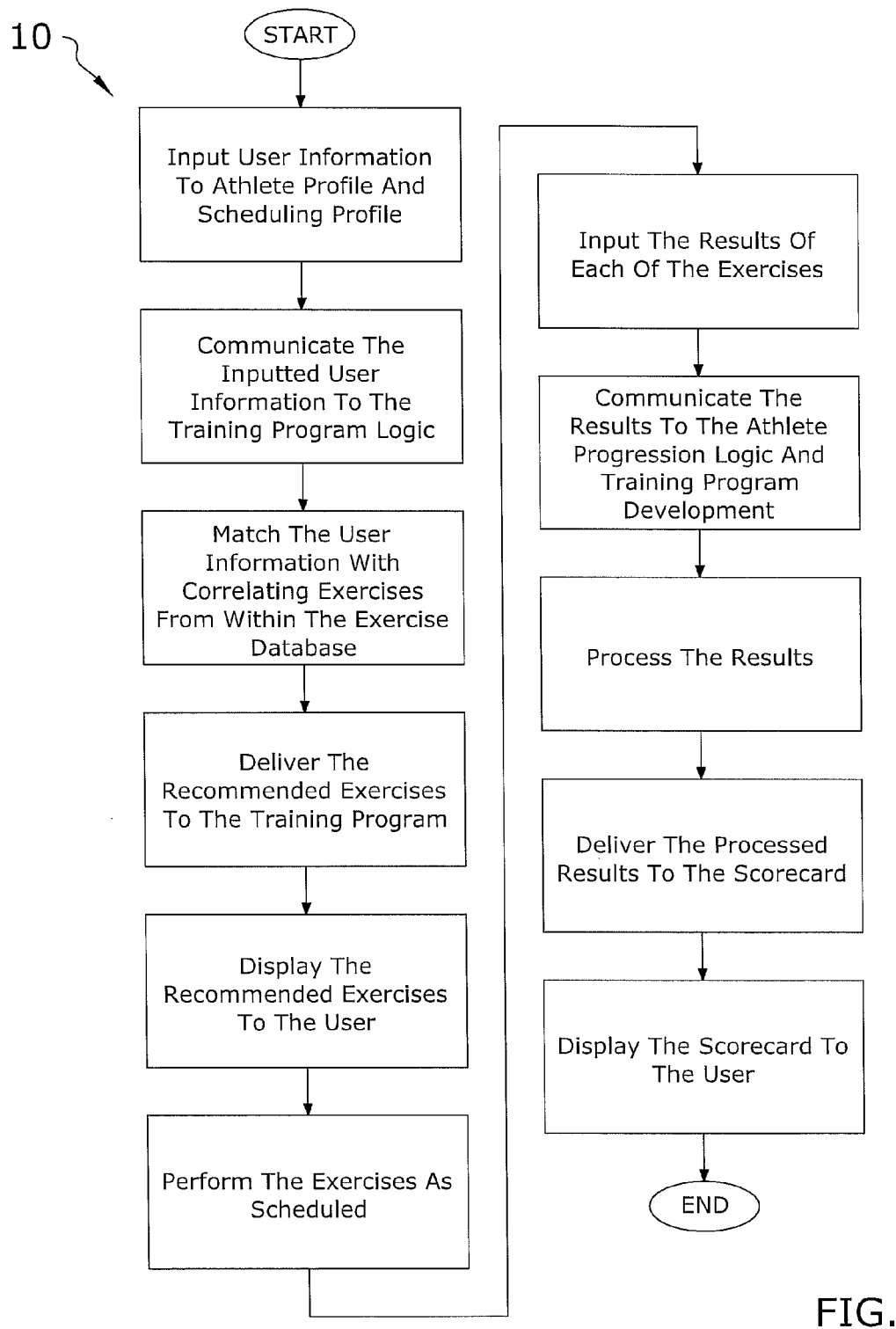
FIG. 5 is a flowchart of the present invention in use.

As illustrated in FIG. 4, the inputted information 21 also generally includes the results of the exercises performed, deemed the results input 50. The results input 50 may include sections for number of drills completed 51, time to complete drills 52, completed drill results, wherein the drills may refer to exercises, training methods, etc. It is appreciated that various other criteria may be included in the results input 50. With the results input 50, users will have a form showing them all drills (exercises) assigned for a particular training period. There will be a field for the users to input the results for each set associated with the exercise, thus depending upon whether the exercise if time-based or rep-based, the user will input a time (seconds) or number completed in the appropriate field of the results input 50 interface.

Also included is the athlete progression logic 65 to compute necessary reports for the input results 50 to be communicated to the user to view progress, goal status, etc. The athlete progression logic 65 generally includes any type of codes, formulas, commands, etc. to process inputted results. The athlete progression logic includes a section 66 for processing results from the results input 50 to be communicated to the scorecard. It is appreciated that various other criteria may be included in the athlete progression logic 65. It is also appreciated that the athlete progression logic 65 may use some or all of the inputted information 21 depending upon the particular input from the user. The athlete progression logic 65 may also be connected to the user database 24, wherein the input results 50 are inputted within the user database 24 or may be directly inputted to the athlete progressive logic 65 and the logic 65 will compare the results 50 to the user database 24 for the athlete profile 30 information.

The athlete progression logic 65 communicates the processed results to a scorecard 90, which may be interactive, viewable online, downloaded, or printed. The scorecard 90 shows a history of completed exercises 91, a comparison of performance 92 illustrating which exercises were performed an amount equal to the recommendation by the training program logic 60 and whether goals were achieved. It is appreciated that various other criteria may be included in the athlete progression logic 65. The athlete progression logic 65 and scorecard 90 represents the athlete's progress by segmenting into key skill categories and groupings. Thereby an athlete can gauge their progress from beginner to master (proficiency level range) on an overall basis or within each skill category as they pertain to the sport. The logic 65 ensures that athlete is progressing through all major skill categories. Athletes may be a beginner in one skill category and proficient in another, but overall proficiency will reflect the lowest skill category proficiency. The proficiency level progression may be illustrated in the scorecard 90 as noted by numeral 93.

In use, the user preferably utilizes the present invention to determine correct exercises for optimizing their performance in a particular sport (e.g. basketball, football, soccer, baseball, martial arts, swimming, skiing hockey, etc.) and increasing their fitness level needed for that particular sport. The user first inputs their user information using the user interface 20 to their athlete profile 30 and scheduling profile 40. The information from the athlete profile 30 and scheduling profile 40 is communicated to the training program logic 60 over the network 16 and matched with correlating exercises within the exercise database 70. The training program logic 60 then communicates the recommended exercises to the training program 80 of the user interface 20 and the user performs the exercises as scheduled.

After performing the exercises, the user inputs the results of each of the exercises, which may include repetitions, time spent, completion percentage, etc. into the input results 50 which is communicated over the network 16 to the athlete progression logic 65 and training program logic 80. The athlete progression logic 65 then processes the results and communicates the processed results to the scorecard 90 which is displayed on the user interface 20 for viewing, printing, or downloading by the user. The user may input results from an exercise to the athlete progressive logic 65 after each exercise or after a set of exercises and may update their schedule 40 or profile 30 at anytime which will automatically adjust their training program 80. The present invention is progressive to keep track of the athlete or user's status as he/she progresses through the training program 80.

Unless otherwise defined, all technical and scientific terms used herein have the same meaning as commonly understood by one of ordinary skill in the art to which this invention belongs. Although methods and materials similar to or equivalent to those described herein can be used in the practice or testing of the present invention, suitable methods and materials are described above. All publications, patent applications, patents, and other references mentioned herein are incorporated by reference in their entirety to the extent allowed by applicable law and regulations.

In case of conflict, the present specification, including definitions, will control. The present invention may be embodied in other specific forms without departing from the spirit or essential attributes thereof, and it is therefore desired that the present embodiment be considered in all respects as illustrative and not restrictive. Any headings utilized within the description are for convenience only and have no legal or limiting effect.

The invention claimed is:

1. A method of using a computer program product, comprising a computer medium having a computer readable program code embodied therein, said computer readable program code is adapted for providing a sports specific training program to an athlete, comprising:
   providing a user interface;
   providing at least one user database operatively connected to said user interface;
   inputting user information into said at least one user database;
   providing an exercise database operatively connected to said user interface, said exercise database having a plurality of targeted exercises, said plurality of targeted exercises each suited for a particular sport and each including exercise information;
   matching said user information from said at least one user database with one or more specific targeted exercises of said plurality of targeted exercises from said exercise database;
   forming a training program comprised of said one or more specific targeted exercises;
   communicating said training program to said user;
   inputting results from performing said one or more specific targeted exercises of said training program;
   dynamically modifying said one or more specific targeted exercises of said training program to reflect a progression of said user through said training program; and
   communicating said modified training program to said user.

2. The method of claim 1, including a network in communication with said user interface for communicating said user information.

3. The method of claim 2, wherein said network is comprised of a global network.

4. The method of claim 1, wherein said user information includes an athlete profile.

5. The method of claim 4, wherein said athlete profile includes an address and contact information portion, a goals and objectives portion, a current and desired position portion, an experience and competition level portion, and a team affiliation portion.

6. The method of claim 1, wherein said user information includes a scheduling profile.

7. The method of claim 6, wherein said scheduling profile includes a user calendar availability, an exercise venue calendar availability, assistance available, and an exercise equipment calendar availability.

8. The method of claim 1, including training program logic to match said user information with said plurality of exercises in said exercise database to determine said one or more targeted exercises.

9. The method of claim 1, wherein said exercise information includes a necessary skill level for each exercise, a recommended frequency to perform each exercise, assistance required for each exercise, equipment and venue required for each exercise, and a time or number required for each exercise.

10. The method of claim 1, wherein said exercise information includes a video and detailed written instructions illustrating each exercise.

11. The method of claim 1, wherein said one or more specific targeted exercises is communicated to said user in an online format.

12. The method of claim 1, wherein said one or more specific targeted exercises is communicated to said user in an electronic file downloadable format.

13. The method of claim 1, wherein said one or more specific targeted exercises is communicated to said user in a printed format.

14. A method of using a computer program product, comprising a computer medium having a computer readable program code embodied therein, said computer readable program code is adapted for providing a sports specific training program to an athlete, comprising:
   providing a user interface;
   providing at least one user database operatively connected to said user interface;
   inputting user information into said at least one user database, said user information relating to a particular sport and said user information including a user experience level relating to said particular sport, user goals relating to said particular sport, and user position relating to said particular sport;
   forming a training program comprised of one or more specific targeted exercises;
   inputting results from performing said one or more specific targeted exercises relating to said inputted user information;
   comparing said inputted results to said inputted user information;
   determining a progression of completion of said one or more specific targeted exercises;
   communicating said progression to said user via a scorecard.

15. The method of claim 14, including a network in communication with said user interface for communicating said user information.

16. The method of claim 15, wherein said network is comprised of a global network.

17. The method of claim 14, wherein said inputted results includes a number of exercises performed and/or the time taken to complete the exercises.

18. The method of claim 14, including athlete progression logic to comparing said inputted results and said inputted user information to an exercise database and overall training program completion requirements to determine how quickly an athlete progresses through the proficiency levels for individual skills and said training program.

19. The method of claim 14, wherein a progress through a proficiency level for individual skills and said training program is communicated to said user in an online, printable, and a downloadable format.

20. A method of using a computer program product, comprising a computer medium having a computer readable program code embodied therein, said computer readable program code is adapted for providing a sports specific training program to an athlete, comprising:

inputting user information to an athlete profile and a scheduling profile of a user;
communicating said inputted user information to a training program logic;
matching said user information with specific exercises of a plurality of exercises from an exercise database;
delivering said specific exercises to a training program;
displaying said specific exercises to said user;
performing said specific exercises;
inputting results of each of said specific exercises;
communicating said results to an athlete progression logic;
processing said results with said athlete progression logic;
delivering said processed results to a progression scorecard; and
displaying said progression scorecard to said user.

* * * * *